United States Patent [19]

Stone

[11] 4,268,101
[45] May 19, 1981

[54] INTEGRAL DOME AND COLLAR ELECTRICAL CONNECTOR

[76] Inventor: Robert D. Stone, 3050 S. Bristol 8N, Santa Ana, Calif. 92704

[21] Appl. No.: 66,564

[22] Filed: Aug. 15, 1979

[51] Int. Cl.³ .............................................. H01R 11/22
[52] U.S. Cl. .................................... 339/61 R; 24/110; 24/216; 339/200 P; 339/DIG. 3
[58] Field of Search ............ 339/45 R, 61 R, 108 TP, 339/200 P, 255 P, 261, DIG. 3, 74 R, 258 A, 259 R; 128/639-644, 783, 798, 802, 803; 24/107, 216, 241 S, 110

[56] References Cited

U.S. PATENT DOCUMENTS

| | | | |
|---|---|---|---|
| 487,389 | 12/1892 | Franke | 24/110 |
| 2,949,530 | 8/1960 | Hagen et al. | 339/258 TC |
| 3,329,851 | 7/1967 | Braeutigam et al. | 339/DIG. 3 |
| 3,862,633 | 1/1975 | Allison et al. | 128/641 |
| 4,040,697 | 8/1977 | Ramsay et al. | 339/61 R |

FOREIGN PATENT DOCUMENTS 558199 12/1943 United Kingdom ........... 339/258 A

*Primary Examiner*—Neil Abrams
*Attorney, Agent, or Firm*—Fulwider, Patton, Rieber, Lee & Utecht

[57] ABSTRACT

There is disclosed an electrical connector for fitting over an elongated axially projecting stem formed with an enlarged-in-diameter button and including a plastic dome jacketing an electrically conductive cap having an integral pair of oppositely disposed peripheral skirts projecting axially in one direction from a flexible transverse top wall. Such skirts are formed on their free extremities with radially inwardly projecting opposed collars which, in the unflexed condition of the top wall, are spaced apart a distance less than the diameter of such button. The top wall may be flexed about a transverse axis to angle the respective skirts outwardly to space such collars transversely apart a distance sufficient to clear such button and a pair of relatively rigid finger grasp ears are disposed on the opposite sides of such transverse axis and project in the axial direction opposite such skirts to be pressed together to flex such top wall and space such collars sufficiently far apart to clear the button. The skirts and top wall may have sufficient flexibility to be snapped over such stem without the necessity of squeezing such ears together.

9 Claims, 6 Drawing Figures

INTEGRAL DOME AND COLLAR ELECTRICAL CONNECTOR

BACKGROUND OF THE INVENTION

1. Field of the Invention:

The present invention relates to electrical contacts and, more particularly, to female electrical contacts of the type that fit over a male electrode which may be affixed to a patient's skin for picking up electrical impulse from the patient.

2. Description of the Prior Art:

In the treatment of a patient, it is frequently desirable to record electrical impulses at various body locations and frequently, male electrodes are affixed to various locations on the patient's body and female electrode connectors are releasably connected therewith for picking up the electrical impulse received by the male electrode for communication to an electrical meter or graph. It is important that the connection between the male and female electrodes are secure once the connection is made and it is desirable that such female connectors be relatively easily disconnected from the male electrode.

Many different meters, such as electrocardiographs, are equipped with different styles of connectors, but most employ a male stem of rather standard construction which incorporates an enlarged-in-diameter button over which the female connector fits to be releasably retained on the male connector. In many instances, when the patient's skin is not unduly sensitive, the female connector merely snaps over the button formed on the male connector stem and is retained thereon by means of a retention spring incorporated in the female connector for resiliently flexing to fit over the button and to be yielding urged radially inwardly beneath the button head to releasably hold the female connector in engagement with the male stem. Connectors of this type are frequently referred to as snap connectors and, while serving the purpose of releasably maintaining electrical connection, suffer the shortcoming that they are relatively expensive to manufacture in that they require assembly of the retention spring within the female connector thus adding to the expense of manufacture and to the likelihood of faulty workmanship which may result in early failure or even inoperability. Furthermore, the juncture points and aperture holes frequently required in the construction of female connectors of this type constitute ideal locations for initiation and maintenance of bacterial growth. Moreover, such connectors are frequently constructed, at least in part, of metal and repeated sterilization thereof and operation in a moist atmosphere frequently results in corrosion which builds up a resistance to electrical conduction, thus detracting from the accuracy of the readout and interfering with smooth connection and disconnection from the male stem and eventually leading to mechanical failure. Thus, it is an object of this invention to provide a female connector which avoids the use of components requiring assembly and forming apertures and juncture points therein and to further provide a female connector that avoids the use of metal components which are subject to corrosion.

In instances, such as post-operative or burn cases, where the patient's skin is unduly sensitive to pain, female connectors providing for frictional operation of a retention spring cannot be employed since the patient cannot tolerate the pain associated with pressing on his skin to make the mechanical connection between the male and female electrodes and, similarly, cannot tolerate the pain associated with pulling on the female connector to disengage the releasable spring frictionally held beneath the male stem button. In these cases, squeeze type female connectors employing ring biased jaws openable by squeezing together projecting handles, are required for different cases and different applications. Not only is the expense of stocking both snap type and squeeze type connectors prohibitive, but many times when squeeze type connectors are required for a test, only snap type connectors are available. Consequently, it is an object of this invention to provide a female connector which is self biased to a closed, engaged position and can be snapped onto and off a male stem and which also incorporates projecting finger grasp ears which may be squeezed by an operator to release the female connector from the male stem without pulling axially on such male stem.

SUMMARY OF THE INVENTION

The connector of the present invention is characterized by a dome incorporating a transversely extending flexible top wall having opposed skirts projecting axially in one direction therefrom and formed on their extremities with inwardly projecting collars spaced apart a distance less than a retention button formed in the male electrode stem. A pair of ears are disposed on the opposite sides of the top wall and project in the axial direction opposite that of the skirts and may be squeezed together to flex the top wall thus spreading the skirts apart and, consequently the collars, to cause such collars to clear the male stem button. In another embodiment, the ears may be eliminated and the connector may be merely snapped onto a male electrode.

DESCRIPTION OF THE DRAWINGS

FIG. 1 is a broken perspective view of a releasable female electrode connector embodying the present invention;

FIG. 2 is an end view of the female electrical connector shown in FIG. 1;

FIG. 3 is a transverse sectional view, in enlarged scale, taken along the line 3—3 of FIG. 1;

FIG. 4 is a broken bottom plan view of the releasable female electrical connector shown in FIG. 1;

FIG. 5 is a transverse sectional view, in enlarged scale, taken along the line 5—5 of FIG. 1; and, FIG. 6 is a transverse sectional view similar to FIG. 5 but showing the connector in its release position.

DESCRIPTION OF THE PREFERRED EMBODIMENT

Figures 1, 2, 3, 4, 5, 6:
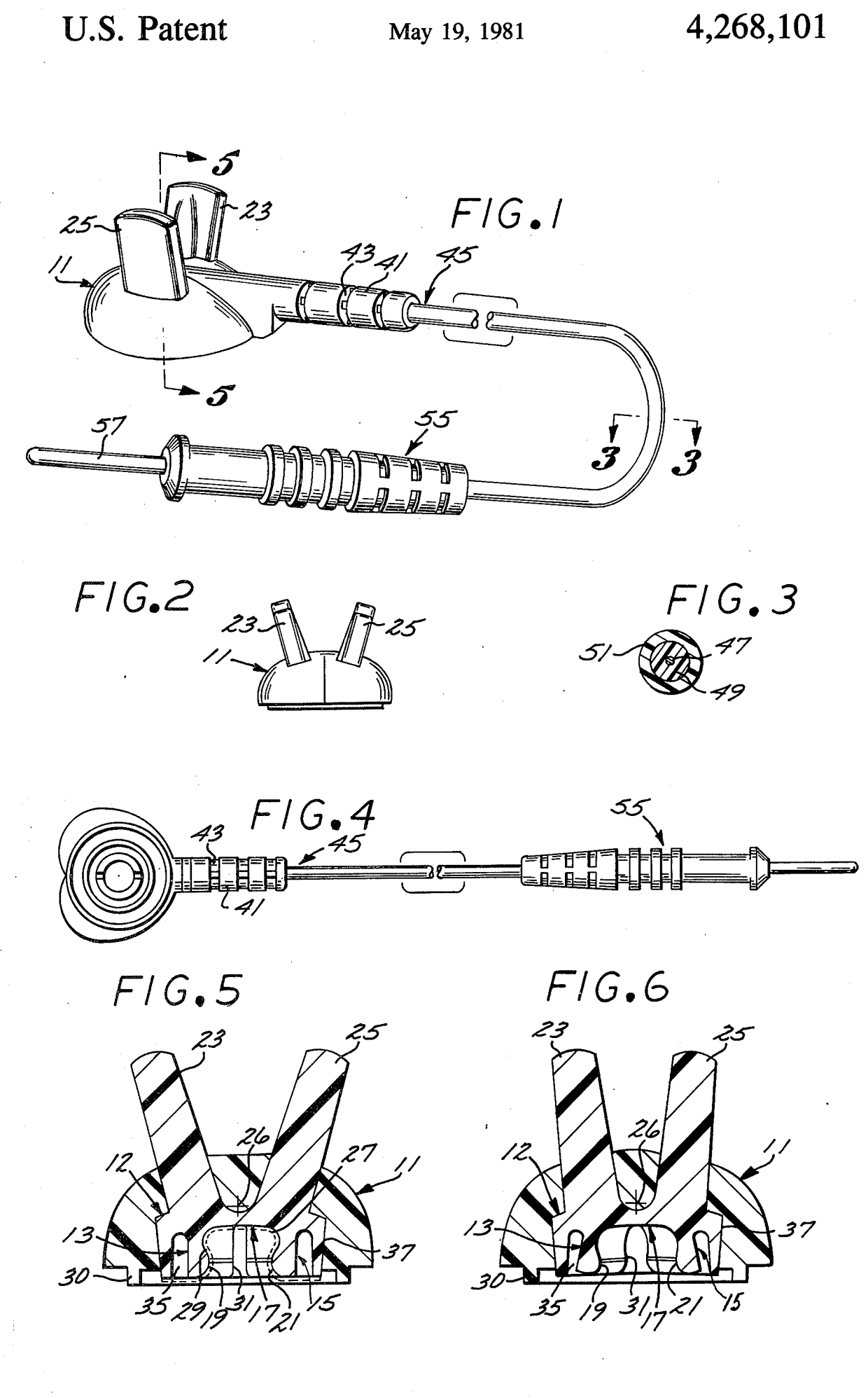

Referring to FIGS. 1 and 5, the integral electrode connector of the present invention includes, generally, a domed jacket 11 covering a hollow electrically conductive connector housing or cap 12, formed with a barrel split on its opposite sides to form a pair of oppositely disposed semi-circular skirts 13 and 15, projecting axially downwardly from a flexible transverse top wall 17. Such skirts are formed on their lower extremities with radially inwardly projecting semicircular collars 19 and 21. Projecting axially upwardly from the flexible wall 17 are a pair of rigid laterally outwardly diverging ears 23 and 25 whereby such ears may be pinched laterally inwardly toward one another to flex the opposite lateral sides of such top wall upwardly and outwardly relative to a transverse intermediate axis 26 to raise the lateral outer portions thereof to angle the semicircular skirts 13 and 15 radially outwardly away from one another to thus spread the collars 19 and 21 apart as shown in FIG. 6 to permit such collars to clear a button 27 formed in the top portion of a axially projecting male electrode 29.

Referring to FIG. 5 in detail, the dome 11 may be constructed of any desirable resilient electrically nonconductive plastic and is heart shaped in transverse cross-section. Such dome 11 surrounds the contact housing 12 and is formed with an axially downwardly projecting circular flange 30 that projects beyond the cap 12 for engaging structure on which the male stem is mounted for maintaining such housing in electrically insulated spaced relationship with respect to such structure. The cap 12 is electrically conductive and the top wall 17 thereof has a memory causing it to assume its unflexed position shown in FIG. 5 to maintain the collars 19 and 21 urged radially inwardly toward one another. It has been found that the housing 12, including the skirts 13 and 15 and ears 23 and 25 may be formed integral with one another and may be constructed of electrically conductive plastic such as 100-41 available from Affey Plastics Corporation, 11 Brent Drive, Hudson, Massachusetts. The skirts 13 and 15 are formed to define therebetween a cavity having a generally circular cross-sectional diameter which is enlarged-in-diameter at its top extremity for receipt of the enlarged-in-diameter male electrode button 27 and then necks down to form the reduced-in-diameter diametrically opposed collars 19 and 21. The circular skirts 13 and 15 are separated by diametrically opposed axial slits 31 which extend throughout the length thereof, terminating at their upper extremities at the top wall 17.

Formed circumferentially around the circular skirts 13 and 15 is a continuous annular groove 35 concentric with such skirts and having formed concentrically therearound an integral circular wall 37.

The ears 23 and 25 are somewhat rectangular in shape and diverge upwardly and outwardly at an angle of approximately 15° to the vertical.

Referring to FIGS. 1 and 3, the dome 11 is formed with a transversely projecting cylindrical boss 41 formed with annular grooves 43 and having a lead assembly 45 projecting thereinto. The lead 45 includes a central tensile strand 47 (FIG. 3) constructed of a high tensile strength material such as beryllium which provides the necessary tensile strength and shares in conducting electrical pulses. The tensile strand 47 is surrounded by a tubular conductor 49 of electrically conductive plastic vinyl which is, in turn, covered by a polyurethane electrical insulator sheath 51. The tubular conductor 49 is in electrical communication on one end with the collars 19 and 21 and the opposite end of the electrical lead 45 is received in a tubular boss, generally designated 55, and formed with an axially projecting electrically conductive male prong 57 receivable in a female receptacle (not shown) of metering equipment which receives the electrical impulses from the connector of present invention. Thus, the male prong 57 is in electrical communication with the semicircular collars 13 and 15 (FIG. 5) and, consequently, with the male electrode stem 29 when connected therewith.

In operation, when the integral female electrical connector of the present invention is to be utilized as a snap connector, the dome 11 may be pressed downwardly over the circular button 27 of a stem 29 and the rounded camming surfaces formed by the bottom of the collars 19 and 21 will engage such button and continued downward pressing thereof will cause such camming surfaces to ride radially outwardly on the opposite sides of such button to flex the lateral outer portions of the top wall 17 upwardly about the intermediate transverse axis 26 (FIG. 6) thus permitting the skirts 13 and 15 to angle outwardly to enable such collars 19 and 21 to clear such button and be urged radially inwardly therebelow. Such connector will thus be held firmly captive on the stem 29 so the low voltage electrical impulses conducted thereinto may be read by the meter to which the prong 57 is connected. When it is desirable to disconnect the female connector of the present invention from the stem 29, the dome 11 may conveniently be grasped by the attendant and drawn axially upwardly to cause the collars 19 and 21 to ride upwardly on the stem 29 to thus be carried apart by the enlarged diameter button 27 to thus clear such button and disengage the stem.

On the other hand, when the female connector of the present invention is to be connected with the electrode stem 29 affixed to the extremity tender skin of a burn patient or the like, it is desirable to avoid pressing downwardly on the button 27 so the attendant will grasp the ears 23 and 25 to press them laterally inwardly toward one another thus rocking such ears inwardly about their base, causing the diametrically outer peripheries of the top wall 17 to flex upwardly about the transverse axis 26 thus enabling the ears 23 and 25 to angle the skirts 13 and 15 laterally outwardly as viewed in FIG. 6. Such outward angling of the skirts 13 and 15 will spread the collars 19 and 21 apart a distance greater than the diameter of the stem button 27 to thus enable the collars to clear the outer peripheries of such stem button so the connector may be fitted down over the stem to register the collars 19 and 21 beneath such button. The ears 23 and 25 may then be released and will be flexed laterally outwardly by the inherent bias of the top wall 17 to thus cause the semicircular skirts 13 and 15 to be urged laterally inwardly to engage the collars 19 and 21 beneath the button 27 thus holding the connector captive on the stem 29. The prong 57 (FIG. 1) will then receive the electrical pulses sensed in the stem 29 to thus give the desired readout. When it is desirable to disconnect the female connector from the stem 29, the ears 23 and 25 may conveniently be grasped and squeezed laterally inwardly toward one another thus again flexing the top wall 17 and enabling the skirts 13 and 15 to be angled laterally outwardly away from one another, thus spreading the collars 19 and 21 apart a distance sufficient to clear the outer peripheries of the stem button 27.

Referring to FIG. 3, it will be appeciated that the coaxial central tensile strand 47 provides the necessary tensile strength for long life of the lead 45 while the electrically conductive polyurethane vinyl 49 provides a low resistance electrically conductive path for communication of the electrical impulses. Such electrically conductive plastic tube, 49 and polyurethane insulator sheet 51 provides a flexible lead which may easily be maintained in a sterilized condition and which inhibits bacterial growth, corrosion and minimizes electrical disturbance of impulses communicated through the conductive tube 49.

From the foregoing it will be apparent that the integral female electrode connector of the present invention provides the convenient, economical and reliable connector which minimizes bacterial growth and which may serve the dual purpose of a snap on and pinch type connector.

I claim:

1. A female electrical connector for fitting over a vertically elongated, electrically conductive electrode stem formed on its top extremity with an enlarged-in-cross section button having a rounded top end, said connector comprising:

a hollow electrically conductive cylindrical cap formed with a stem-receiving chamber for telescoping over said stem and including a flexible top wall and a downwardly projecting barrel split longitudinally along its diametrically opposite sides to form opposed axially projecting semicylindrical skirts, said skirts being formed on their free extremities with radially inwardly projecting collars for fitting radially inwardly under the opposite sides of such button to releasably lock said cap on such stem, said collars tapering upwardly and radially inwardly to form respective downwardly facing cam surfaces, said top wall having a relaxed position and being sufficiently flexible to enable its laterally opposite sides disposed on the opposite sides of the axial plane of the splits in said barrel to be angled upwardly and outwardly from such plane of said splits to a pinch-release position angling said skirts downwardly and radially outwardly at an angle sufficient to space said collars a radial distance outwardly from one another to cause the radial inner peripheries thereof to clear the opposite sides of said button;

laterally spaced apart elongated finger grasp ears mounted on said top wall on the lateral opposite sides of such plane of said splits and projecting longitudinally upwardly for being grasped and on their upper extremities and pinched together to flex said top wall to said pinch-release position; and, an electrical lead leading from said top wall whereby when it is desirable to snap said cap onto said button, it may be pressed thereagainst from an axial direction causing said cam surfaces of said respective collars to engage the opposite sides of said top end of said button to thus cause said collars, and consequently, the lower extremities of said skirts to be spread radially apart and when said collars clear said button said top wall will flex to said relaxed position to urge such bottom extremities of said skirts radially inwardly to snap said collars radially inwardly under the opposite sides of such button and when it is desirable to pinch release said connector from such stem, the free extremities of said ears may be pinched together to cause said top wall to flex to said pinch-release position to spread said collars apart to clear the exterior dimension of said button.

2. An electrical connector as set forth in claim 1 wherein:
said ears are formed integral with said top wall.

3. An electrical connector as set forth in claim 1 wherein:
said ears and skirts are integral with one another and are formed of electrically conductive material.

4. An electrical connector as set forth in claim 1 wherein:
said lead includes a central high tensile conductive strand surrounded by a tubular electrically conductive plastic conductor and an electrically insulative sheath encasing said conductor.

5. An electrical connector as set forth in claim 1 wherein:
said ears are axially aligned at their bases with said respective skirts and are integral therewith.

6. An electrical connector as set forth in claim 1 wherein:
skirts and collars are formed integral with one another and are constructed of electrically conductive plastic.

7. An electrical connector as set forth in claim 1 that includes:
an electrically insulative dome covering said top wall and formed with an exterior peripheral wall surrounding said barrel.

8. An electrical connector as set forth in claim 1 that includes:
a flexible electrically insulative jacket fitted over said cap and ears.

9. An electrical connector as set forth in claim 1 wherein:
said skirts are flexible and said cap is covered with a flexible, electrically insulative jacket.

* * * * *